United States Patent
He et al.

(10) Patent No.: US 10,550,692 B2
(45) Date of Patent: Feb. 4, 2020

(54) FLUID CHARACTERIZATION AND PHASE ENVELOPE PREDICTION FROM DOWNHOLE FLUID SAMPLING TOOL

(71) Applicant: Halliburton Energy Services, Inc., Houston, TX (US)

(72) Inventors: Tian He, Houston, TX (US); Mehdi Alipour Kallehbasti, Humble, TX (US); Ming Gu, Humble, TX (US); Christopher Michael Jones, Houston, TX (US); Darren Gascooke, Houston, TX (US); Michael T. Pelletier, Houston, TX (US); Di Du, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/546,531

(22) PCT Filed: Aug. 11, 2016

(86) PCT No.: PCT/US2016/046605
§ 371 (c)(1),
(2) Date: Jul. 26, 2017

(87) PCT Pub. No.: WO2018/031022
PCT Pub. Date: Feb. 15, 2018

(65) Prior Publication Data
US 2019/0017377 A1    Jan. 17, 2019

(51) Int. Cl.
    E21B 49/08    (2006.01)
(52) U.S. Cl.
    CPC ...... *E21B 49/081* (2013.01); *E21B 2049/085* (2013.01)

(58) Field of Classification Search
CPC .................. E21B 49/081; E21B 2049/085
See application file for complete search history.

(56) References Cited

U.S. PATENT DOCUMENTS

| 7,526,953 B2 | 5/2009 | Goodwin et al. |
| 2007/0137292 A1* | 6/2007 | Xian ............... G01N 33/2823 73/152.18 |

(Continued)

FOREIGN PATENT DOCUMENTS

| WO | 2010071619 | 6/2010 |
| WO | 2012094007 | 7/2012 |

(Continued)

OTHER PUBLICATIONS

Applications of Equations of State in the Oil and Gas Industry, Thermodynamics—Kinetics of Dynamic Systems by Ashour et al dated Sep. 22, 2011.

(Continued)

*Primary Examiner* — Manuel L Barbee
(74) *Attorney, Agent, or Firm* — Benjamin Fite; C. Tumey Law Group PLLC

(57) ABSTRACT

Disclosed herein are methods and systems for fluid characterization of fluid samples from a downhole fluid sampling tool. A fluid characterization method may include obtaining a fluid sample of a reservoir fluid; analyzing the fluid sample to derive input parameters, wherein the input parameters comprise fluid properties obtained from measurement of the fluid sample; determining component mole fractions of the fluid sample using a mole fraction distribution function; and determining calculated fluid properties using equation of state flash calculating.

18 Claims, 12 Drawing Sheets

(56) References Cited

U.S. PATENT DOCUMENTS

| | | | |
|---|---|---|---|
| 2011/0088949 A1* | 4/2011 | Zuo | E21B 49/08 |
| | | | 175/48 |
| 2011/0284219 A1 | 11/2011 | Pomerantz et al. | |
| 2012/0296617 A1 | 11/2012 | Zou et al. | |
| 2014/0316705 A1 | 10/2014 | Zuo et al. | |
| 2015/0167456 A1 | 6/2015 | Irani | |

FOREIGN PATENT DOCUMENTS

| | | |
|---|---|---|
| WO | 2013022556 | 9/2013 |
| WO | 2015134043 | 9/2015 |
| WO | 2015138805 | 9/2015 |

OTHER PUBLICATIONS

International Search Report and Written Opinion for Application No. PCT/US2016/046605 dated May 1, 2017.
Equation-of-State-Based Downhole Fluid Characterization by Zuo et al, SPE Journal, dated Mar. 2011.

* cited by examiner

FLUID CHARACTERIZATION AND PHASE ENVELOPE PREDICTION FROM DOWNHOLE FLUID SAMPLING TOOL

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves obtaining and analyzing fluid samples from a reservoir of interest. There are a variety of different tools that may be used to obtain the fluid sample. The fluid sample may then be analyzed to determine fluid properties, including, without limitation, component concentrations, molecular weight, molecular weight distribution, gas-oil ratios, bubble point, dew point, phase envelope, viscosity, combinations thereof, or the like. Conventional analysis has required transfer of the fluid samples to a laboratory for analysis. Downhole analysis of the fluid sample may also be used to provide real-time fluid properties, thus avoiding delays associated with laboratory analysis. Surface wellsite analysis may also be used to provide real-time fluid properties without the need for transfer of the fluid samples to a laboratory. However, accurate determination of fluid properties in real-time may be limited in certain circumstances, such as during the early stages of field development (e.g., exploration/appraisal) when there is limited, or potentially even no data.

BRIEF DESCRIPTION OF THE DRAWINGS

These drawings illustrate certain aspects of some of the embodiments of the present invention, and should not be used to limit or define the invention.

DETAILED DESCRIPTION

Figure 1:
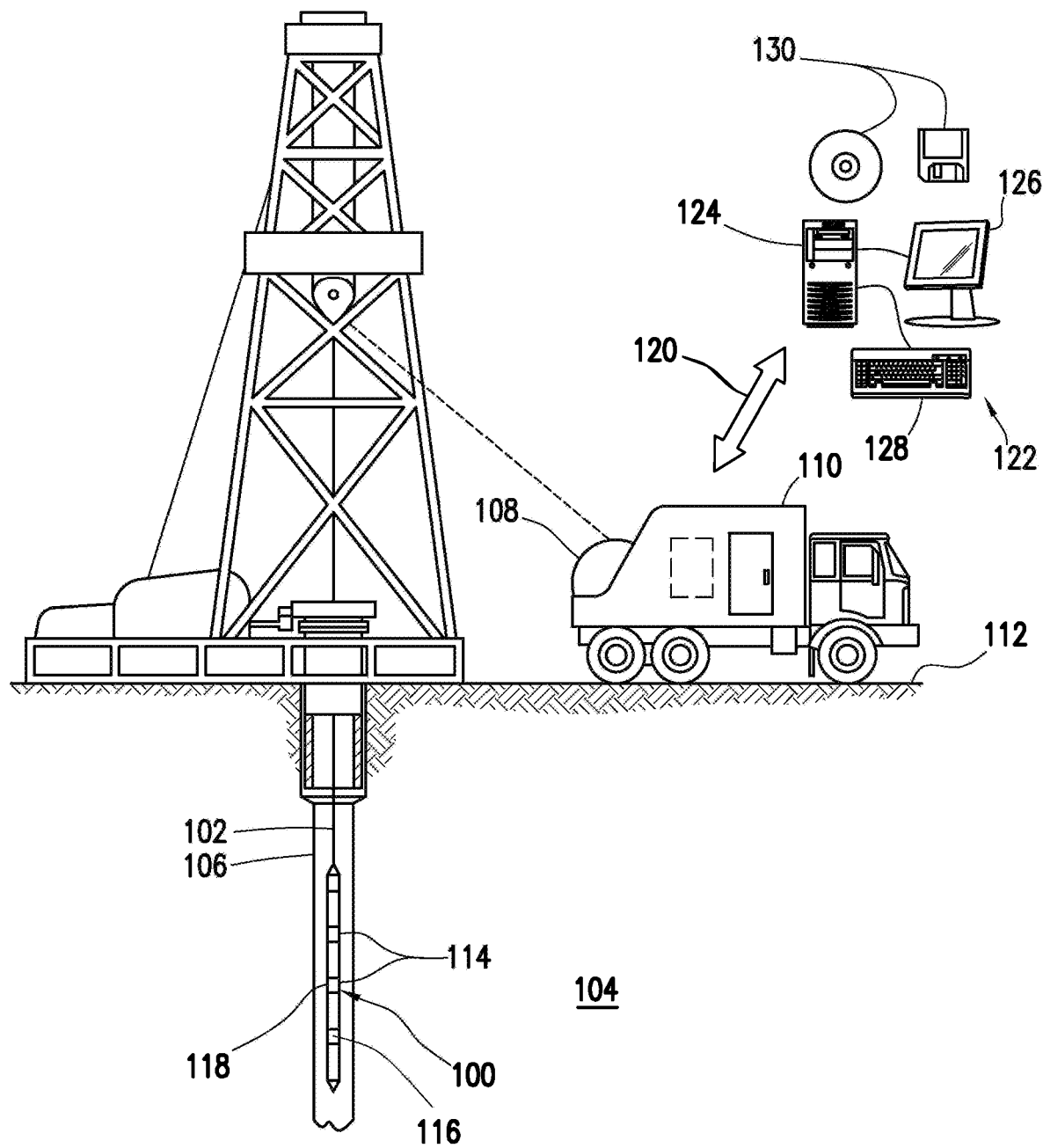
FIG. 1 is a schematic diagram of an example downhole fluid sampling tool on a wireline.

Disclosed herein are methods and systems for fluid characterization of fluid samples from a downhole fluid sampling tool. The fluid characterization may include a determination of the component concentrations, including a delumped component concentration. By way of example, the delumped component concentration may include a mole distribution of the components of the fluid sample, including plus fractions (e.g., C6+) that may ordinarily be lumped together. The methods and systems may further include generation of pressure-volume-temperature properties (e.g., bubble point, phase envelop prediction, etc.) of the fluid samples based on the fluid characterization. As will be discussed in more detail below, the methods and systems for fluid characterization may use a distribution function in conjunction with an equation of state to determine component concentrations of the fluid samples. Inputs may include downhole measurements of the fluid sample, including, without limitation, gas-oil ratio, live oil density, and/or bubble point.

Characterization of reservoir fluids may be desired in a number of circumstances. Reservoir fluids may contain a number of different components, including hydrocarbons and non-hydrocarbons, of varying molecular weights, which may make accurate determination of component concentration in real-time difficult. Measurements of a fluid sample of the reservoir fluid may be taken that can provide component concentrations, which are typically provided in composition of lighter hydrocarbons with heavier hydrocarbons (C5+, C6+, etc.) lumped together. By way of example, the component concentration may be provided showing fractions of carbon dioxide ($CO_2$), methane ($CH_4$), ethane ($C_2H_6$), propane ($C_3H_8$), butane ($C_4H_{10}$), pentane ($C_5H_{12}$), and the C6+ alkane group. The C6+ group may include the concentration of all hydrocarbons with six or more carbon atoms lumped into a single component concentration. In some instances, the C5 hydrocarbons may not be separately reported, with the C5+ hydrocarbon group lumped into a single component concentration. Moreover, some of the lower hydrocarbons, such as the C3, C4, or C5 hydrocarbons may also be grouped and reported together, for example, C3-C4 hydrocarbon group, C3-C5 hydrocarbon group, and/or C4-C5 hydrocarbon group. These concentrations may be provided as weight or mole percentages.

However, the lumped component concentration may need to be split, for example, to provide a delumped component concentration. Using the delumped component concentration, pressure-volume-temperature properties (e.g., bubble point, phase envelop prediction, etc.) of the fluid sample may be determined, which may be more accurate than if the lumped component concentration, or another technique is used for this determination. By having these fluid properties, information may be used to determine the quantity and quality of hydrocarbons in a reservoir and to develop or modify strategies for hydrocarbon production. Disclosed herein are methods and systems for fluid characterization that can provide component concentrations, including delumped component concentrations, from a lumped component concentration. The delumped component concentrations may include mole distribution of components, including for plus fractions (e.g., C5+, C6+), which may then be used to determine additional fluid properties, such as pressure-volume-temperature properties.

FIG. 1 is a schematic diagram of an example of a downhole fluid sampling tool 100 on a wireline 102. The downhole fluid sampling tool 100 may be used to obtain a fluid sample, for example, a fluid sample of a reservoir fluid from subterranean formation 104. The fluid sample may then be analyzed as described herein to determine a fluid characterization that includes component concentrations. As illustrated, a wellbore 106 may extend through subterranean formation 104. While the wellbore 106 is shown extending generally vertically into the subterranean formation 104, the principles described herein are also applicable to wellbores that extend at an angle through the subterranean formation 104, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run downhole fluid sampling tool 100 into wellbore 106. Hoist 108 may be disposed on a recovery vehicle 110. Hoist 108 may be used, for example, to raise and lower wireline 102 in wellbore 106. While hoist 108 is shown on recovery vehicle 110, it should be understood that wireline 102 may alternatively be disposed from a hoist 108 that is installed at surface 112 instead of being located on recovery vehicle 110. Downhole fluid sampling tool 100 may be suspended in wellbore 106 on wireline 102. Other conveyance types may be used for conveying downhole fluid sampling tool 100 into wellbore 106, including coiled tubing and wired drill pipe, for example. Downhole fluid sampling tool 100 may comprise a tool body 114, which may be elongated as shown on FIG. 1. Tool body 114 may be any suitable material, including without limitation titanium, stainless steel, alloys, plastic, combinations thereof, and the like. Downhole fluid sampling tool 100 may further include one or more sensors 116 for measuring properties of the fluid sample, reservoir fluid, wellbore 106, subterranean formation 104, or the like. The downhole fluid sampling tool 100 may be used to collect fluid sample from subterranean formation 104. The downhole fluid sampling tool 100 may obtain and separately store different fluid samples from subterranean formation 104.

The downhole fluid sampling tool 100 may further include a fluid analysis module 118. The fluid analysis module 118 may be operable to derive properties and characterize the fluid sample. By way of example, the fluid analysis module 118 may measure absorption spectra and translate such measurements into component concentrations of the fluid sample, which may be lumped component concentrations, as described above. The fluid analysis module 118 may also measure gas-to-oil ratio, live fluid density, live fluid viscosity, formation pressure, and formation temperature. The fluid analysis module 118 may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 118 may include random access memory (RAM), one or more processing units, such as a central processing unit (CPU), or hardware or software control logic, ROM, and/or other types of nonvolatile memory.

Any suitable technique may be used for transmitting signals from the downhole fluid sampling tool 100 to the surface 112. As illustrated, a communication link 120 (which may be wired or wireless, for example) may be provided that may transmit data from downhole fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. Information handling system 122 may be disposed on recovery vehicle 110 or otherwise positioned at surface 112. The information handling system 122 may act as a data acquisition system and possibly a data processing system that analyzes information from downhole fluid sampling tool 100. For example, information handling system 122 may process the information for fluid characterization of fluid samples from downhole fluid sampling tool 100, including a determination of the component concentrations, for example. The information handling system 122 may also determine additional properties of the fluid sample, such as pressure-volume-temperature properties (e.g., bubble point, phase envelop prediction, etc.) based on the fluid characterization. This processing may occur at surface 112 in real-time. Alternatively, the processing may occur at surface 112 or another location after recovery of downhole fluid sampling tool 100 from wellbore 106. Alternatively, the processing may be performed by an information handling system in wellbore 106, such as fluid analysis module 118. The resultant fluid characterization and fluid properties may then be transmitted to surface 112, for example, in real-time.

Figure 2:
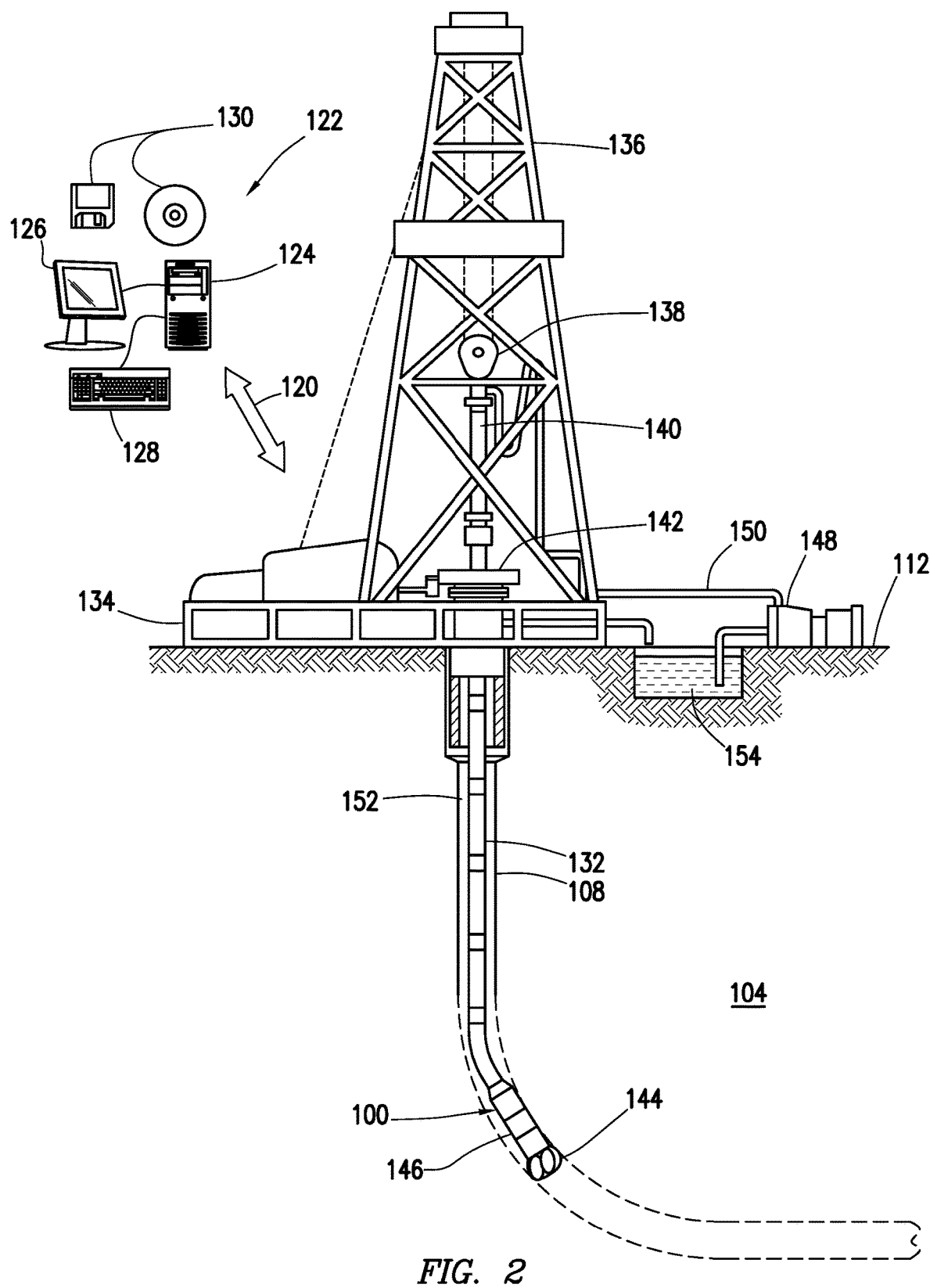
FIG. 2 is a schematic diagram of an example downhole fluid sampling tool on a drill string.

Referring now to FIG. 2, a schematic diagram is shown of downhole fluid sampling tool 100 disposed on a drill string 132. As illustrated, wellbore 106 may extend through subterranean formation 104. Downhole fluid sampling tool 100 may be similar in configuration and operation to downhole fluid sampling tool 100 shown on FIG. 1 except that FIG. 2 shows downhole fluid sampling tool 100 disposed on drill string 132. It should be noted that while FIG. 2 generally depicts a land-based drilling system, those skilled in the art will readily recognize that the principles described herein are equally applicable to subsea drilling operations that employ floating or sea-based platforms and rigs, without departing from the scope of the disclosure.

As illustrated, a drilling platform 134 may support a derrick 136 having a traveling block 138 for raising and lowering drill string 132. Drill string 132 may include, but is not limited to, drill pipe and coiled tubing, as generally known to those skilled in the art. A kelly 140 may support drill string 132 as it may be lowered through a rotary table 142. A drill bit 144 may be attached to the distal end of drill string 132 and may be driven either by a downhole motor and/or via rotation of drill string 132 from the surface 112. Without limitation, drill bit 144 may include, roller cone bits, PDC bits, natural diamond bits, any hole openers, reamers, coring bits, and the like. As drill bit 144 rotates, it may create and extend wellbore 106 that penetrates various subterranean formations 104. A pump 148 may circulate drilling fluid through a feed pipe 150 to kelly 140, downhole through interior of drill string 132, through orifices in drill bit 144, back to surface 112 via annulus 152 surrounding drill string 132, and into a retention pit 154.

Drill bit 144 may be just one piece of a downhole assembly that may include one or more drill collars 146 and downhole fluid sampling tool 100. Downhole fluid sampling tool 100, which may be built into the drill collars 146) may gather measurements and fluid samples as described herein. As previously described, information from downhole fluid sampling tool 100 may be transmitted to an information handling system 122, which may be located at surface 112. As illustrated, communication link 120 (which may be wired or wireless, for example) may be provided that may transmit data from downhole fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. In addition to, or in place of processing at surface 112, processing may occur downhole (e.g., fluid analysis module 118 on FIG. 1).

Figure 3:
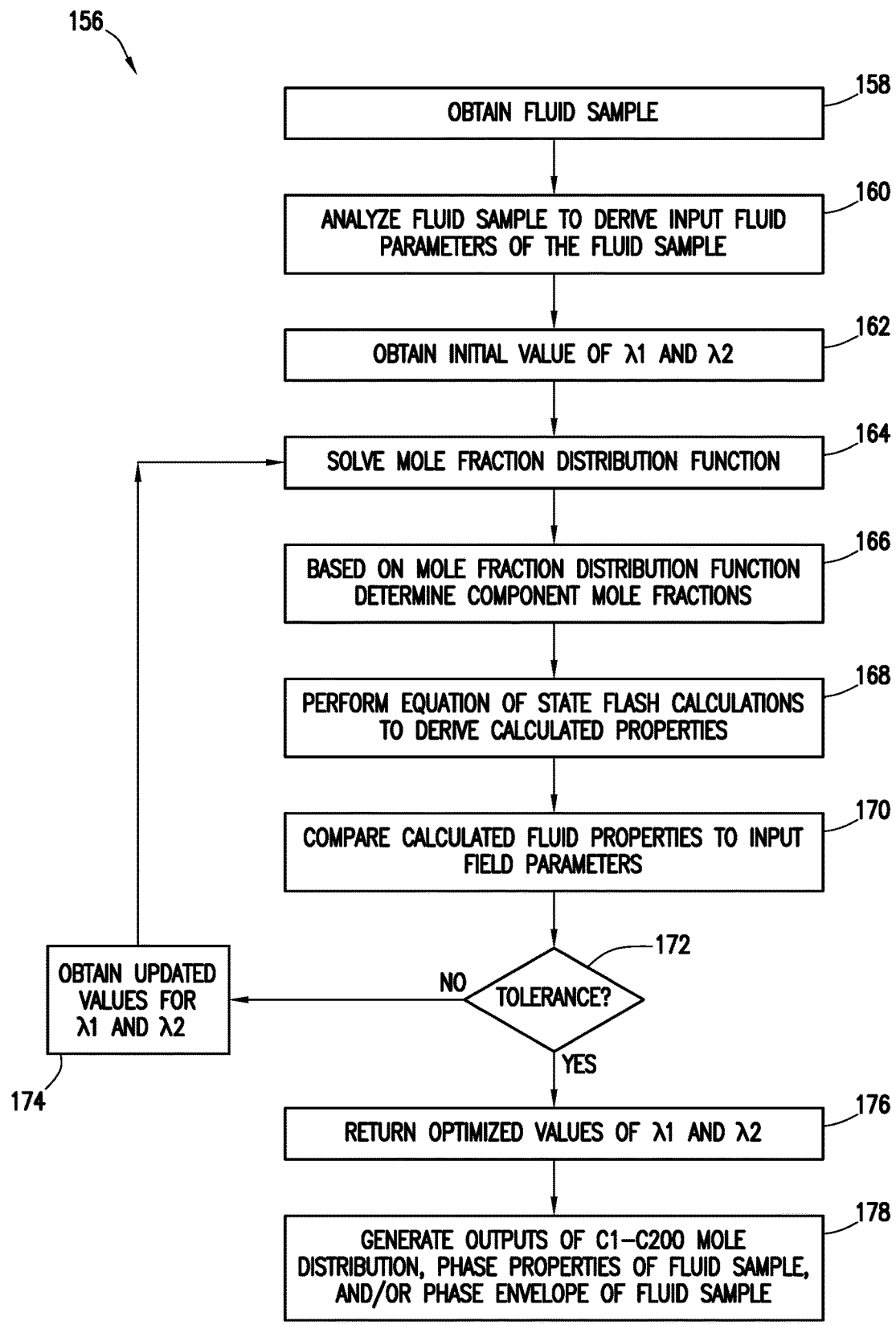
FIG. 3 is a flow chart of an example fluid characterization method.

FIG. 3 shows a flow chart of an example of a fluid characterization method 156. The fluid characterization method 156 may be implemented using the systems implemented on FIGS. 1 and 2, for example, to characterize the fluid properties of a fluid sample. The fluid characterization method 156 may be implemented at surface 112 or in wellbore 106. By way of example, fluid analysis module 118 of downhole fluid sampling tool 100 may include a processing unit (e.g., a microprocessor, etc.) that can be operable to implement one or more of the method steps of fluid characterization method 156. By way of further example, information handling system 122 may also include a processing unit 124 (e.g., a microprocessor, etc.) that can be operable to implement one or more of the method steps of fluid characterization method 156. As will be appreciated, processing may occur either in wellbore 106, at surface 112, at a remote location, or a combination of these locations.

In step 158, a fluid sample may be obtained. The fluid sample may be a fluid sample from a reservoir of interest, for example, from subterranean formation 104 shown on FIGS. 1 and 2. Any suitable technique may be used to obtain fluid sample. As described previously, downhole fluid sampling tool 100 may be used to collect fluid sample on a wireline 102 (e.g., FIG. 1) or on a drill string 132 (e.g., FIG. 2), for example. For example, downhole fluid sampling tool 100 may be operated to obtain a fluid sample. The fluid sample may be obtained at formation temperature and pressure. It should be understood that downhole fluid sampling tool 100 is merely illustrative of one example apparatus that may be used in obtaining a fluid sample and those of ordinary skill in the art should be able to select an appropriate apparatus and associated methodology to obtain a fluid sample. The fluid sample need not necessarily be collected downhole. By way of example, the techniques described herein may be used to characterize the fluid sample of a produced fluid that may be obtained at surface 112. After fluid sample is obtained, subsequent processing steps (e.g., steps 160 to 178) may occur at surface 112 or in wellbore 106. Alternatively, fluid sample may be transferred to a remote location for one or more of the subsequent processing steps.

In step 160, the fluid sample may be analyzed to derive input parameters that characterize the fluid sample. Without limitation, the input parameters may be obtained from measurements of the fluid sample. The measurements may be performed in wellbore 106, at surface 112, or at a remote location. The downhole fluid sampling tool 100 or other suitable formation evaluation tools may be used to analyze the fluid sample. Any measuring instrument capable of producing a measurable response to the change of the fluid property may be used. The measuring instrument may contain a detector and/or sensor detecting, for example, density, resistivity/conductivity, viscosity, chromatography, radioactivity, dielectric constant, optical density, magnetic resonance, weight, acoustic impedance, acoustic velocity, optical response, diffusion coefficients, molecular weight, refractive index at various wavelengths, and combinations thereof. One or more sensors or detectors may be used in the measuring instrument.

The input parameters of the fluid sample that may be derived may include fluid properties that may be obtained from measurements of the fluid sample, including, without limitation, one or more of component concentrations (e.g., weight %, etc.), gas-to-oil ratio, live oil density (or dead oil density) and bubble point. Additional fluid properties that may be derived may include one or more of volume fraction of water, API gravity, live oil viscosity, formation temperature, or formation pressure, among others. As previously described, the component concentrations obtained from these measurements may typically be a lumped component concentration with concentration of heavier hydrocarbons lumped together. By way of example, the component concentration may be provided showing fractions of carbon dioxide ($CO_2$), methane ($CH_4$), ethane ($C_2H_6$), propane ($C_3H_8$), butane ($C_4H_{10}$), pentane ($C_5H_{12}$), and the C6+ group. The C6+ group may include the concentration of all hydrocarbons with six or more carbon atoms lumped into a single component concentration. In some instances, the C5 hydrocarbons may not be separately reported, with the C5+ hydrocarbon group lumped into a single component concentration. Moreover, some of the lower hydrocarbons, such as the C3, C4, or C5 hydrocarbons may also be grouped and reported together, for example, C3-C4 hydrocarbon group, C3-C5 hydrocarbon group, and/or C4-C5 hydrocarbon group. These concentrations may be provided as weight or mole percentages. "Live oil" typically refers to an oil at reservoir conditions. A fluid sample at reservoir conditions may be referred as "live oil." The live oil density of the fluid sample may be obtained from measurements at reservoir conditions. Without limitation, the live oil density may be obtained using a density sensor, for example, on downhole fluid sampling tool 100. The bubble point is the temperature and pressure at which the first bubble of gas comes out of the fluid sample. Without limitation, the bubble point may be obtained downhole measurements. Without limitation, the gas-to-oil ratio may be obtained by measuring the quantity of vapor components and liquid components of crude oil using near infrared absorption peaks. The ratio of vapor components to the oil peak may be directly related to gas-to-oil ratio.

In step 162, initial values for molecular weight of C6+ components ($\lambda 1$) and density of C36+ components ($\lambda 2$) may be obtained. The molecular weight of C6+ components ($\lambda 1$) and density of C36+ components ($\lambda 2$) may be two unknowns that are determined using fluid characterization method 156. Using these values, component concentrations of the fluid sample, including a delumped component concentration, may be determined. The initial values for molecular weight of C6+ components ($\lambda 1$) and density of C36+ components ($\lambda 2$) may derived using the input parameters obtained in step 160 from analysis of fluid sample.

Figure 4:
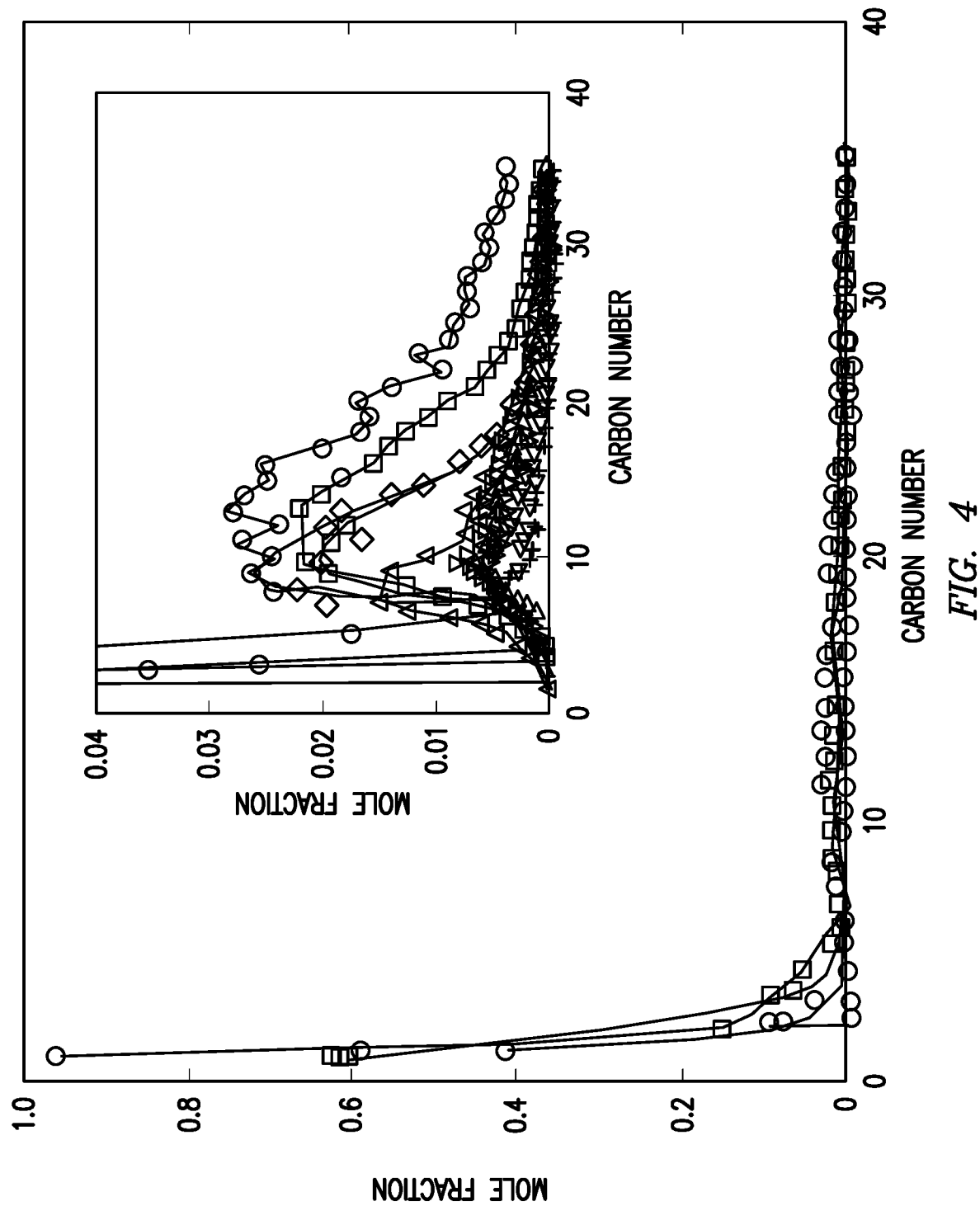
FIG. 4 is chart of single carbon number mole fraction distribution of different live oil samples, wherein the inset shows a zoomed-in view of the C5 to C36 plus components.
Figure 5:
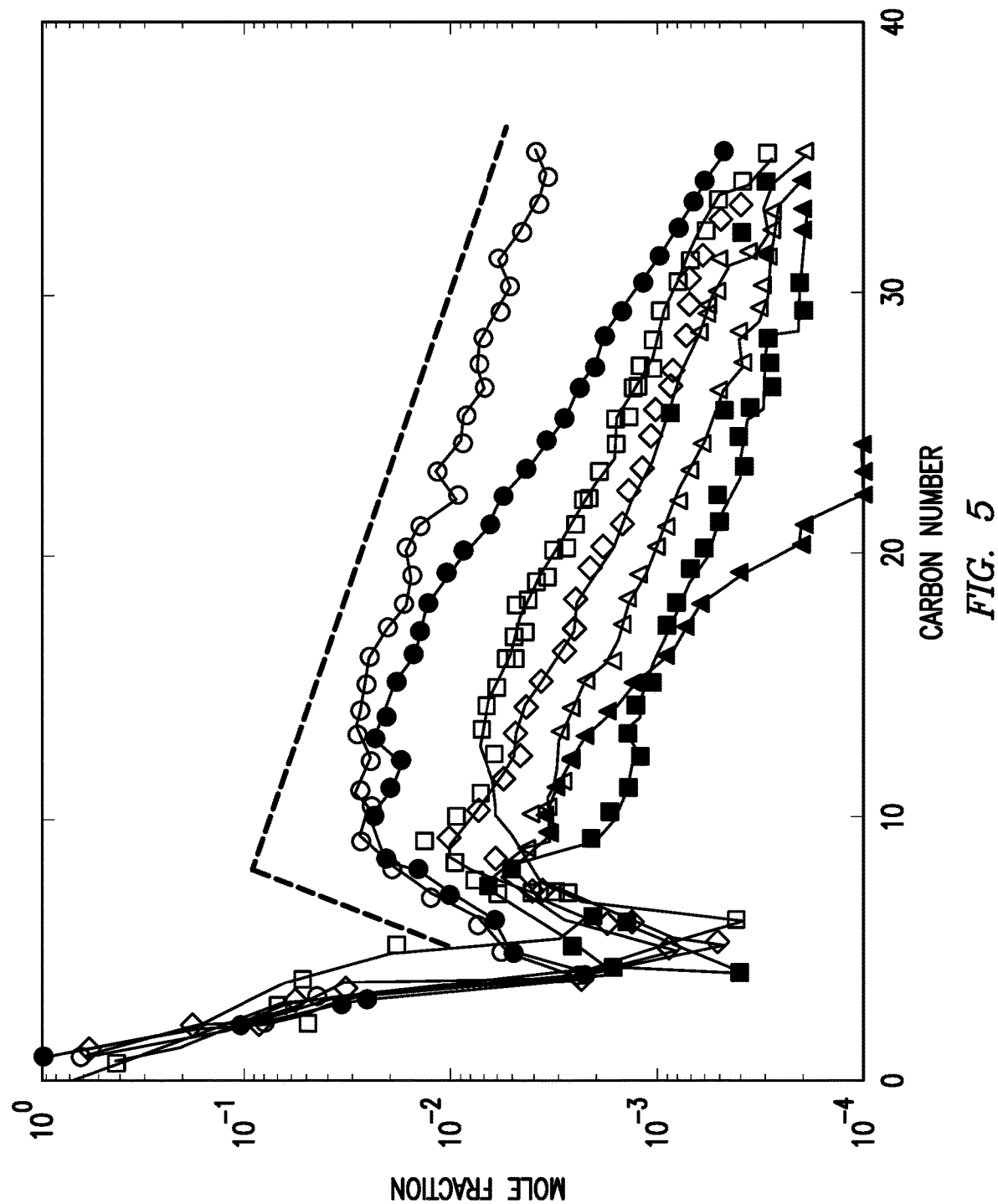
FIG. 5 is a chart of the logarithm of the single mole fraction distribution shown on FIG. 4.
Figure 6A:
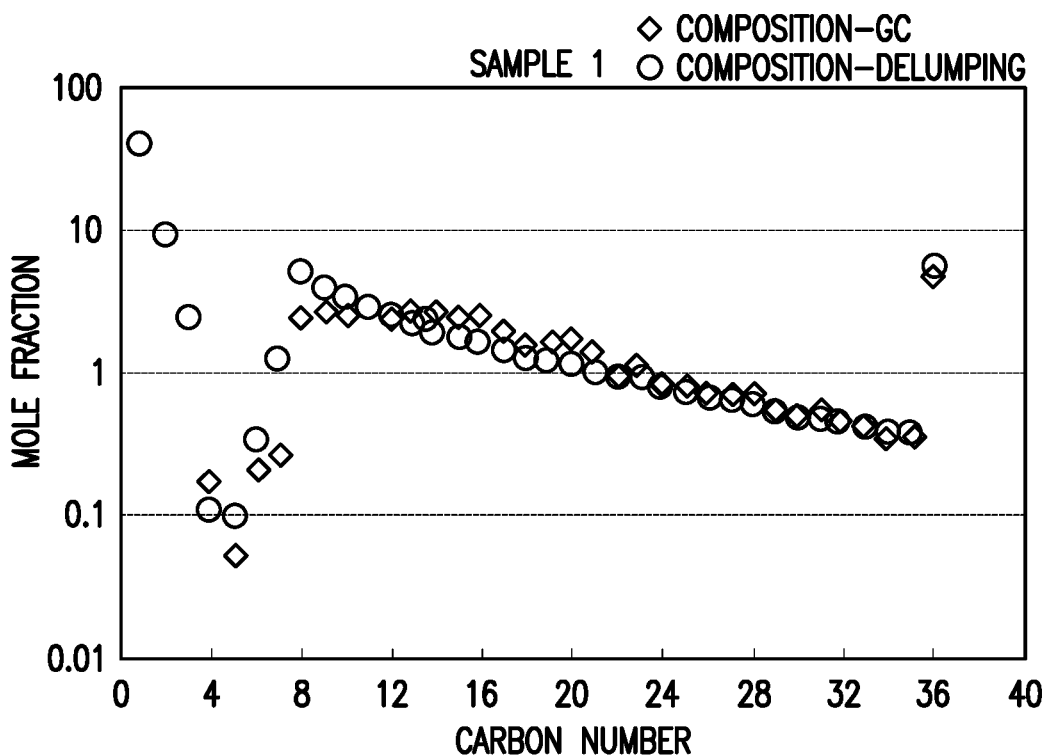
FIGS. 6A to 6F are comparisons of delumped and gas chromatograph mole fraction distributions for different oil samples.
Figure 6B:
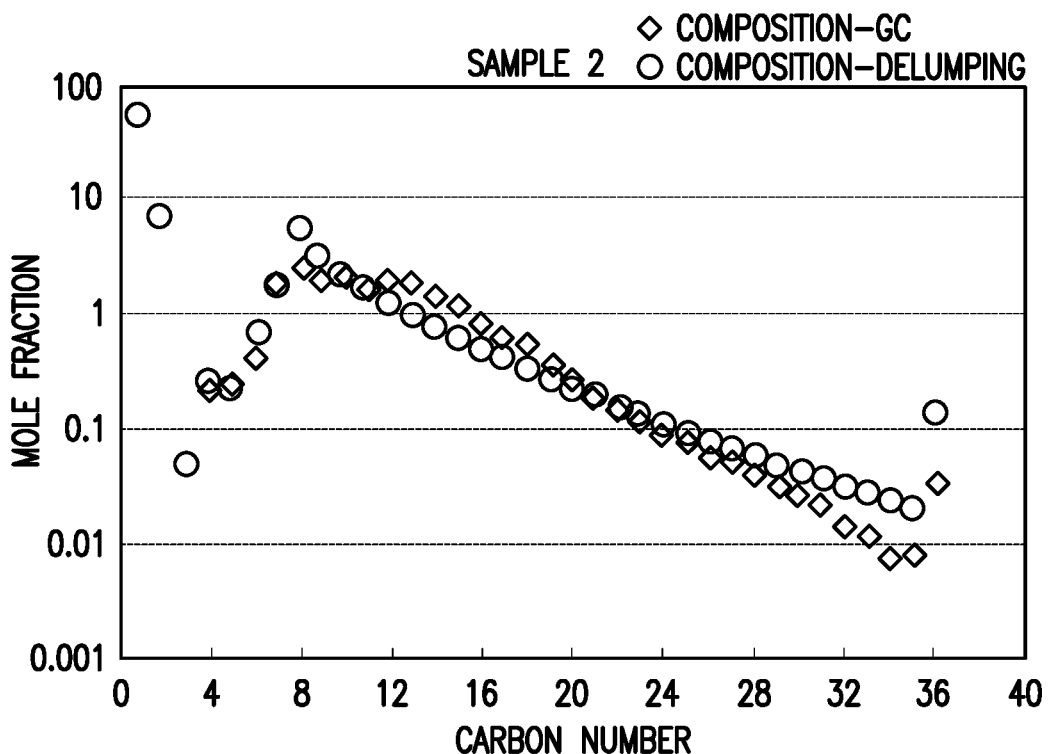
Figure 6C:
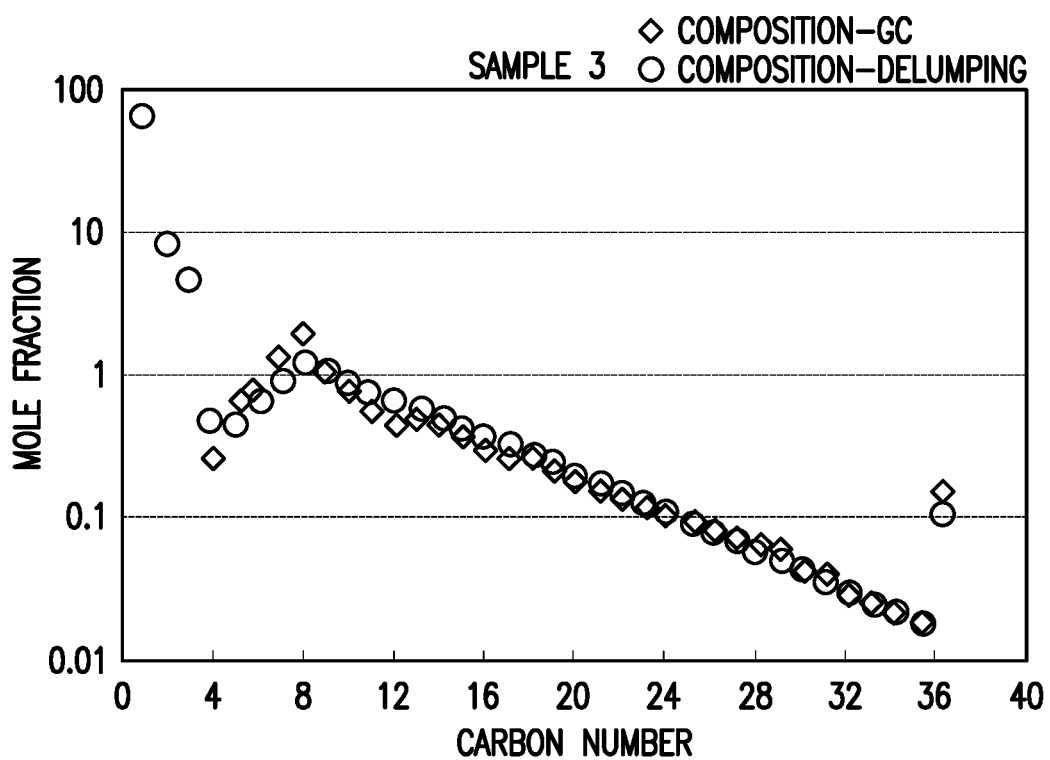
Figure 6D:
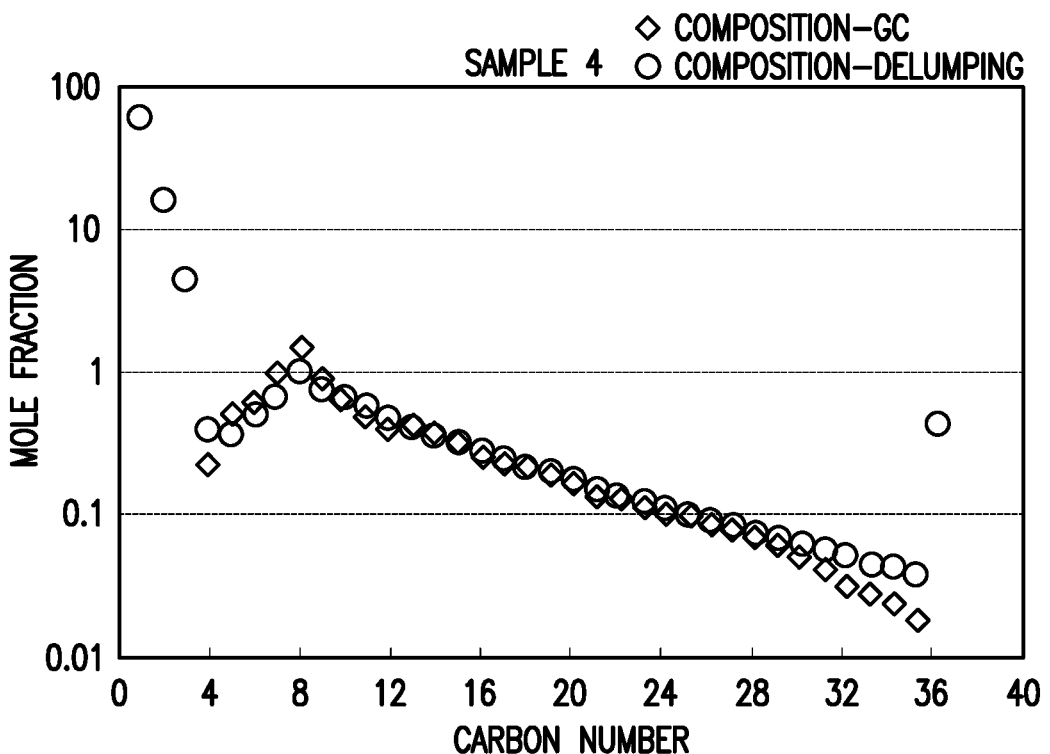
Figure 6E:
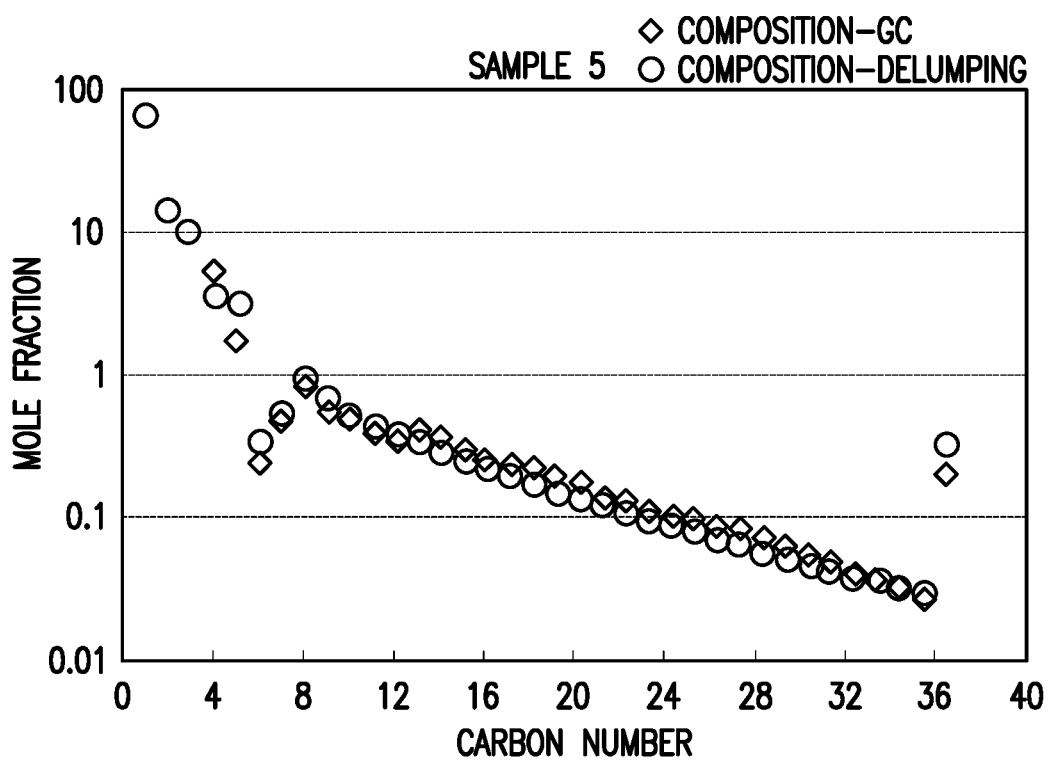
Figure 6F:
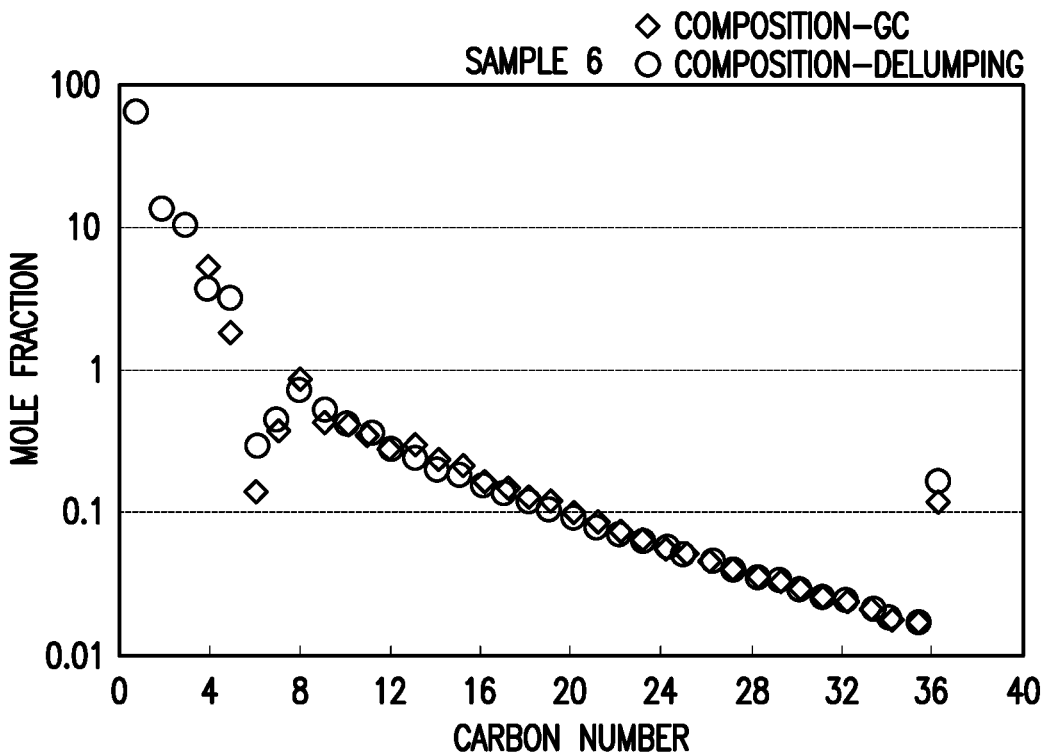
Figure 7A:
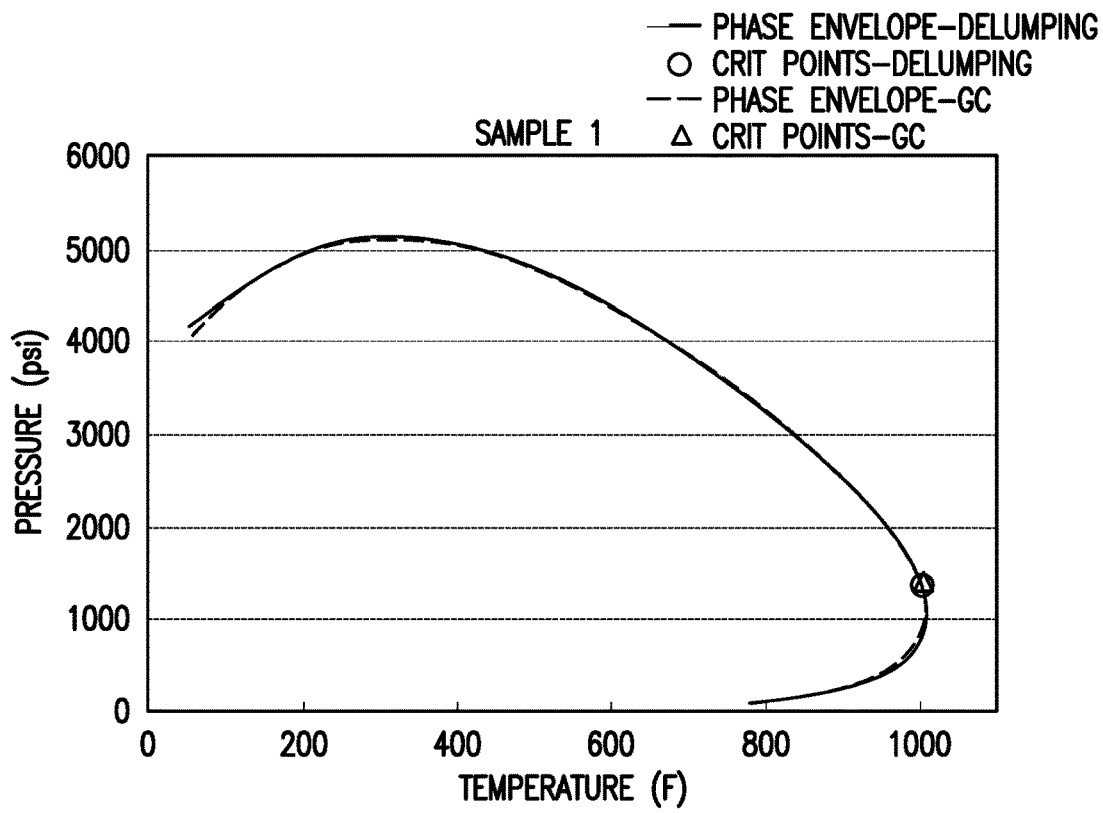
FIGS. 7A to 7F are comparisons of phase envelopes predicted from delumped and gas chromatograph mole fraction distributions for different oil samples.
Figure 7B:
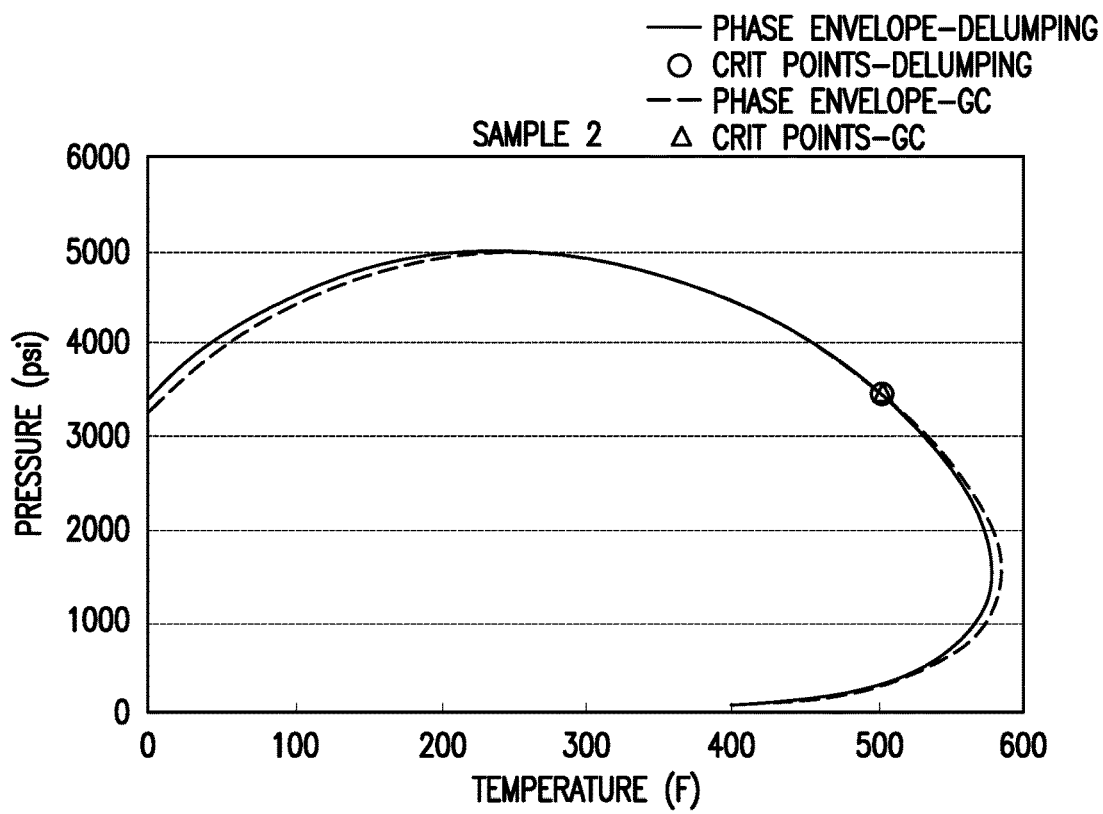
Figure 7C:
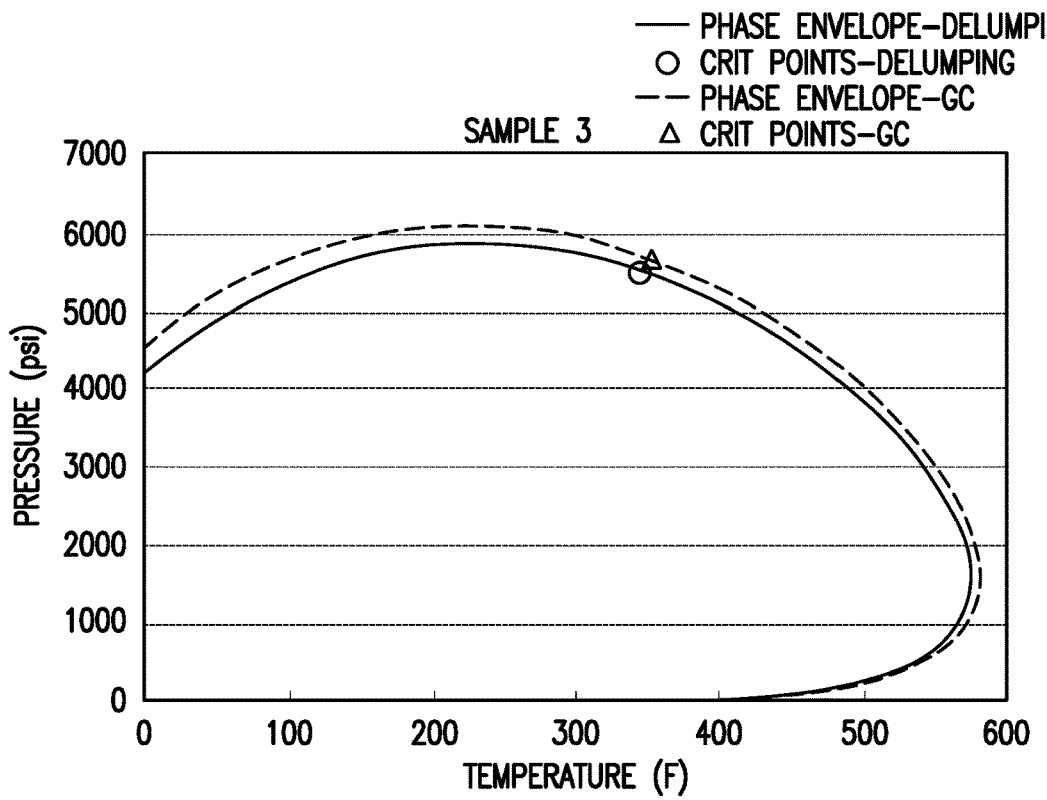
Figure 7D:
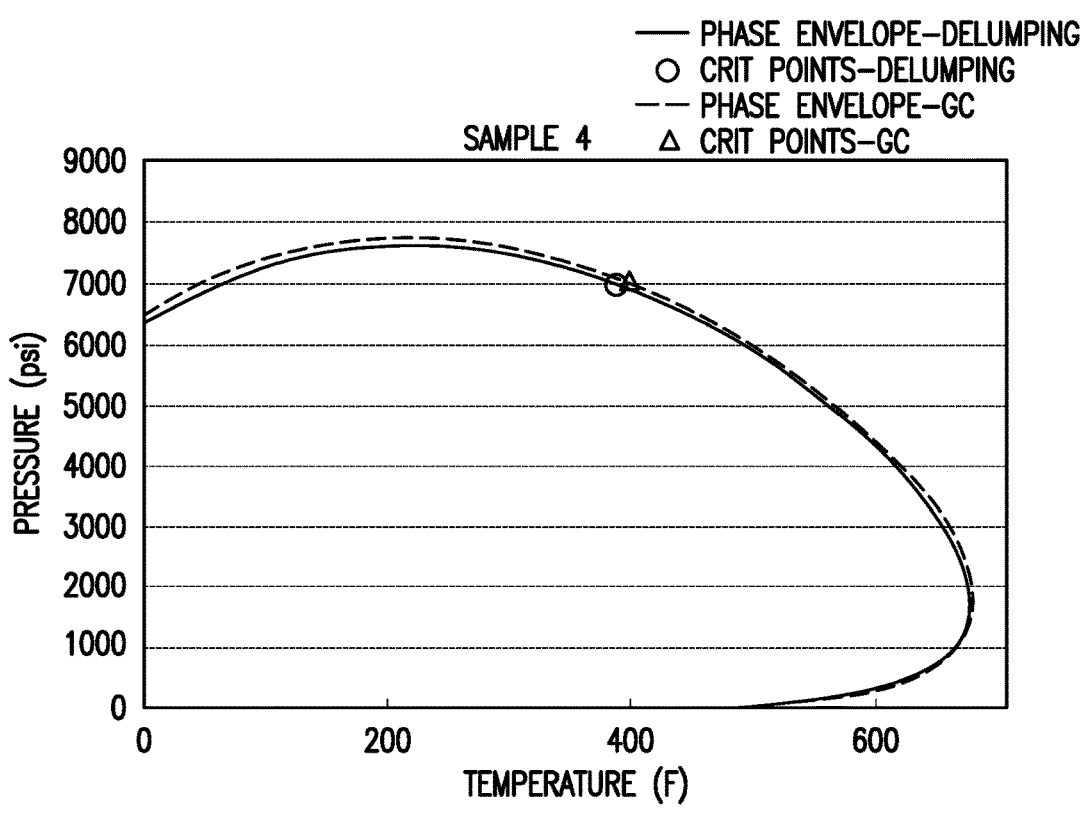
Figure 7E:
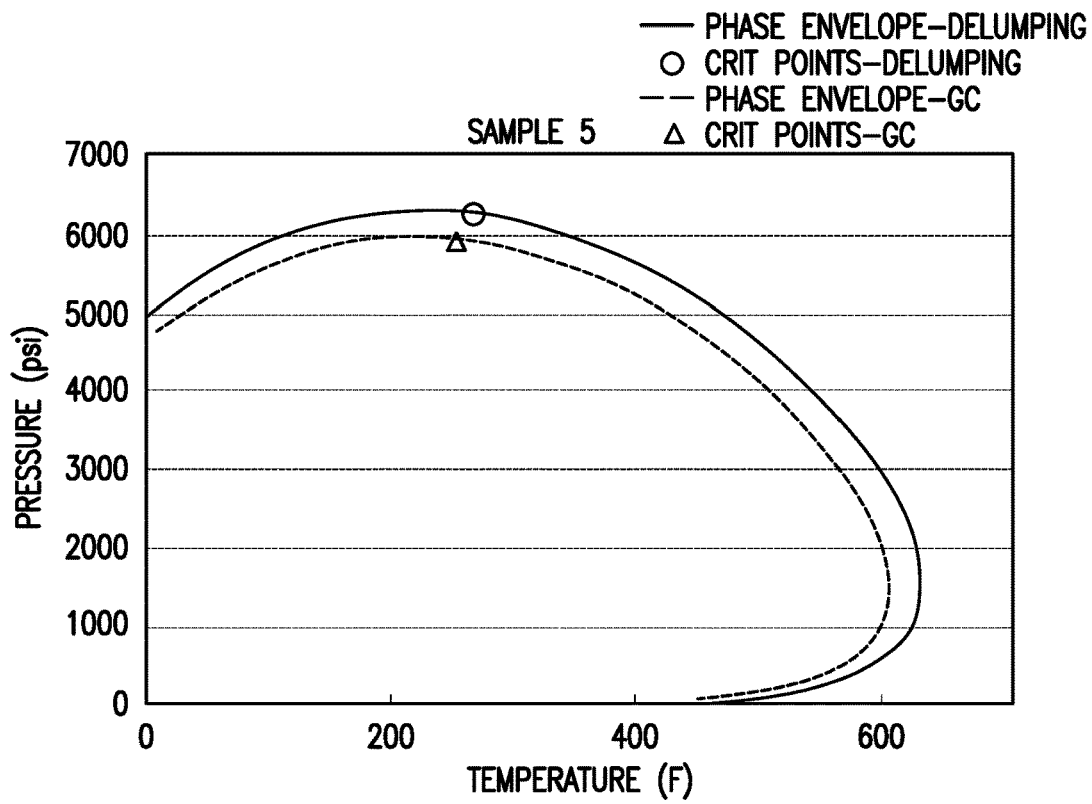
Figure 7F:
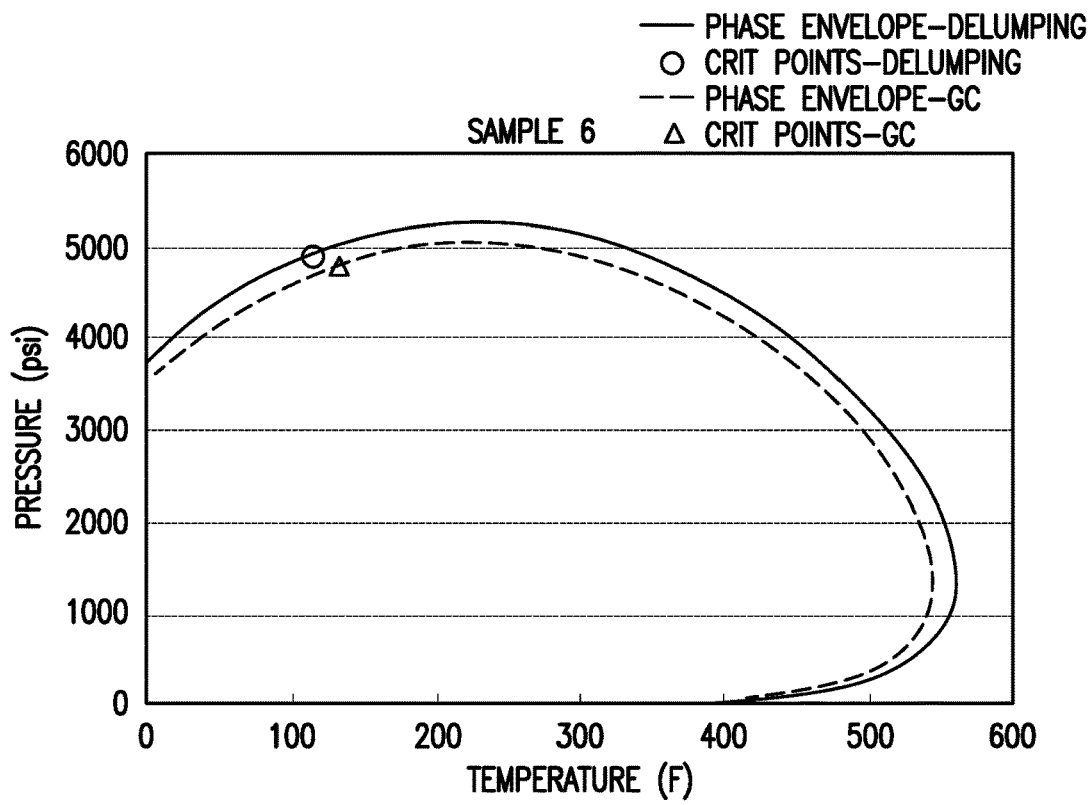
Figure 8:
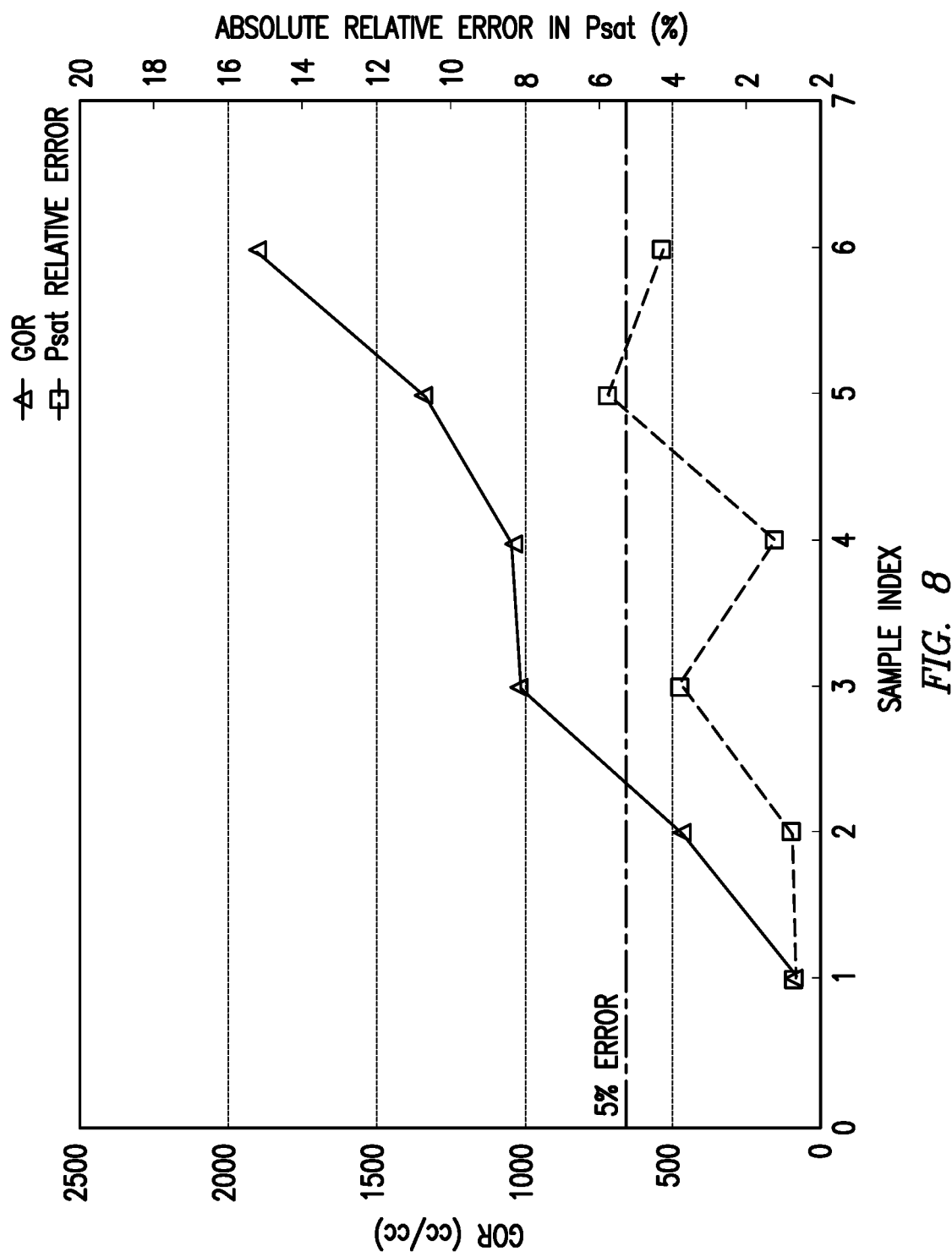
FIG. 8 is a chart of relative error between saturated pressure at 250° F. predicted from the delumped and gas chromatograph mole fraction distributions.

Next, a mole fraction distribution function may be used to determine component mole fractions of the fluid sample. In step 164, the mole fraction distribution function may be solved and, in step 166, the component mole fractions of the fluid sample may be determined based on the mole fraction distribution function. The mole fraction distribution function may characterize reservoir fluid as a function of mole fraction of different components of the fluid. FIG. 4 shows a live oil single carbon number mole fraction distribution for a number of fluid samples. As illustrated, the mole fraction distribution is provided on FIG. 4 for over ten light oil/gas condensate samples based on lab gas chromatography and distillation results. As illustrated, all the samples have a maximum fraction at C1, which may be due to the nature of light oil, for example. The mole fraction then declines dramatically with increasing carbon number. However, another increase is observed at C5 until a secondary maximum may be achieved at C8. Then the mole fraction decreases towards a plateau of zero. The exponential increasing trend from C5 to C8 and exponential decreasing trend from C8 to C36+ may be observed in FIG. 5, which is a semi-log plot of FIG. 4. Based on these observations, a split exponential distribution function may be used as the mole fraction distribution function as follows:

$$z_i = \begin{cases} \sigma e^{-\tau_1(k-i)^{\alpha_1}}, & i = 5, \ldots, k \\ \sigma e^{-\tau_2(i-k)^{\alpha_2}}, & i = k, \ldots, 200 \end{cases} \quad (1)$$

In equation 1, $z_i$ is the mole fraction of component with carbon number i and k is the single carbon number with the local maximum mole fraction, which may vary for different fluid samples. For the group of samples shown on FIGS. 4 and 5, k=8~13. $\sigma$, $\tau$, and $\alpha$ are parameters to be solved for certain samples, wherein $\sigma$ is a scaling parameter to tune a total mole fraction of C5 to C200 and $\tau$ and $\alpha$ are parameters to tune the increasing and decreasing trends (e.g., concavity of the curves). The subscripts 1 and 2 in equation 1 denote the increasing and decreasing regions, respectively. The subscript i represents the single carbon number.

In step 164, the mole fraction distribution function may be solved. As previously described, the mole fraction distribution function may characterize the single carbon number as a function of mole fraction for a fluid sample. The mole fraction distribution function may include one more unknown parameters that may need to be solved to characterize the component mole fractions of a fluid sample. By way of example, equation 1 includes five unknown parameters ($\sigma$, $\tau_1$, $\tau_2$, $\alpha_1$, and $\alpha_2$) that need to be solved for before component mole fractions may be determined. One or more constraints may be used for determining the unknown parameters in the mole fraction distribution function. Five constraints may be needed for solving equation 1 as there are five unknown parameters. The basis of the constraints that may be used for the mole fraction distribution function may include, without limitation, mole balance, mass balance, the continuity nature of the functions, or combinations thereof. The constraints may also include theoretical assumptions, semi-empirical assumptions, or empirical assumptions. Thus, determining the unknown parameters may be a semi-empirical or empirical determination. Accordingly, in step 64, the mole fraction distribution function (e.g., equation 1) may be solved to determine the unknown parameters.

In step 166, the mole fraction distribution function may be used to determine component mole fractions. Without limitation, with the unknown parameters of the mole fraction distribution function known, the mole fraction distribution function may be used to determine the C1-C200 component. By way of example, the component mole fractions determined from the mole fraction distribution function may be a delumped component concentration that includes mole distribution of components, including for plus fractions (C5+, C6+, etc.). Where equation 1 may be used, the mole fraction or $z_i$ (i=1 to 200) of the sample fluid may be obtained.

In step 168, equation of state flash calculations may be performed to derive calculated fluid properties. The equation of state flash calculations may be carried out over the component mole fractions determined in step 166. To reduce the computational complexity, the component mole fractions may be lumped, for example, to C1, C2, . . . , C34, C35, and C36+ mole fractions. The calculated fluid properties determined by the equation of state flash calculations may include one or more of gas-to-oil ratio or dead oil density, for example. "Dead oil" typically refers to an oil at sufficiently low pressure that it contains substantially no dissolved gas or relatively thick oil that has lost its volatile components. Additional calculated fluid properties may include, but should not be limited to, liquid mole fraction distribution, vapor mole fraction distribution, density, molecular weight and mole volume of the liquid and vapor portion of the live oil.

The flash calculations may be based on equation of state equations that represent the functional relationship between pressure, volume, and temperature of the fluid sample. Equations of states may be used to predict physical properties, such as macroscopic pressure-volume-temperature properties, including bubble point, dew point, phase envelope, viscosity, density, combinations thereof, Equation of state flash calculations may use information or properties such as temperature, pressure, and composition. For example, one simple equation of state is PV=nRT, known as the ideal gas law, where P=pressure, V=volume, n=moles, R=Ideal Gas Constant (also used for units conversion), and T=absolute temperature (Kelvin or Rankine). When the physical properties and composition of the reservoir fluid under a given set of conditions are known, the behavior of the reservoir fluid at other pressures and temperatures may be predicted. Equations of state that may be used may include, for example, expansions of the ideal gas law to account for individual molecular compositions. According to some embodiments, they are third order equations. Any of a variety of equations of state may be used. The equation of state may be cubic or non-cubic. The equation of state may vary depending on or more compositional components of the fluid sample. The equations of state have many names, as they have been modified to improve the match between predicted and observed behavior. Without limitation, the equation of state may be selected from one or more of Boyle, Van der Waals, Redlich-Kwong, Soave-Redlich-Kwong, Peng-Robinson, Peng-Robinson-Stryjek-Vera, Patek-Teja, Schmit-Wenzel, or Esmaeilzadeh-Roshanfekr.

In step 170, the calculated fluid properties may be compared to the input fluid parameters. As described above, the input fluid parameters may be derived from analysis of the fluid sample in step 160. By way of example, gas-to-oil ratio and live oil density may be measured. From the live oil density, the dead oil density may be determined. The calculated fluid properties may also include a calculated gas-to-oil ratio and a calculated dead oil density. Without limitation, this comparison may include comparing the calculated gas-to-oil ratio with the input gas-to-oil ratio obtained from fluid analysis in step 160. Without limitation, this comparison may further include comparing the calculated gas-to-oil ratio ad the dead oil density derived from input obtained from fluid analysis in step 160.

A tolerance error may be used, step 172, to determine if another iteration through the mole fraction distribution function (steps 162 to 170) and the equation of state flash calculations (step 168) may be required. The tolerance error may be a small value selected to impact the iteration number and total calculation time, but should have minimal impact on the final results. Without limitation, if the relative differences between the input fluid parameters and the calculated fluid parameters are not within a tolerance error, then another iteration may be required. By way of example, if the relative difference between the calculated gas-to-oil ratio and input gas-to-oil ratio and between the calculated dead oil density and dead oil density derived from the input dead oil density, are not within a tolerance error, then another iteration may be required. If the tolerance error determines that another iteration may be required, values for molecular weight of $C_{6+}$ components ($\lambda 1$) and density of $C_{36+}$ components ($\lambda 2$) may be updated (step 174) and steps 164 to 172 may be repeated. Updating values for the molecular weight of $C_{6+}$ components ($\lambda 1$) and density of $C_{36+}$ components ($\lambda 2$) may utilize any of a variety of different analysis algorithms, including, without limitation, Newton-Raphson method. The iteration of steps 164 to 172 may be repeated with values for the molecular weight of $C_{6+}$ components ($\lambda 1$) and density of $C_{36+}$ components ($\lambda 2$) may be obtained until values for the comparison of step 170 or within the tolerance error of step 172.

When the tolerance error of step 172 may be satisfied, the fluid characterization method 156 moves to step 176 and optimized values for the molecular weight of $C_{6+}$ components ($\lambda 1$) and density of $C_{36+}$ components ($\lambda 2$) for the fluid sample may be returned. In block 178, the optimized values may result in optimized values may be used to generate an output of component mole fractions (e.g., C1-C200 mole distributions) and pressure-volume-temperature properties, such as bubble point and phase envelop prediction, among others. Without limitation, the optimized values may be used to calculate the output values for component mole fractions (e.g., C1-C200 mole distributions) and pressure-volume-temperature properties. The component mole fractions may be a delumped component mole fractions. The delumped mole fractions may comprise component mole fractions for each carbon number from C1 to C200. Alternatively, the delumped component mole fractions may be expanded, but may continue to have some of the heavier hydrocarbons lumped into a group. For example, ten, twenty, thirty, or even more component mole fractions may be provided for C5+ hydrocarbons.

The techniques disclosed herein for fluid characterizations, such as fluid characterization method 156 may be performed in real-time. "Real time" performance refers to "on the fly" fluid characterization accomplished during field use of downhole fluid sampling tool 100 (or other tool), as opposed to prior to the field use or post to the field use, e.g., performance in real time, such as while logging, without retrieving the downhole fluid sampling tool 100 or fluid sample from downhole. Performance of the fluid characterization in real time may allow a user to determine component mole fractions and phase envelope prediction at or about the same time as measurements are made.

Without limitation, the preceding techniques may be used in a variety of methods and systems for characterizing a fluid sample. An example of a fluid characterization method may comprise obtaining a fluid sample of a reservoir fluid; analyzing the fluid sample to derive input parameters, wherein the input parameters comprise fluid properties obtained from measurement of the fluid sample; determining component mole fractions of the fluid sample using a mole fraction distribution function; and determining calculated fluid properties using equation of state flash calculating. An example of a system for characterizing a fluid sample may comprise a downhole fluid sampling tool operable to obtain fluid samples while disposed in a wellbore; and a processing unit operable to analyze the fluid sample to derive input parameters, wherein the input parameters comprise fluid properties obtained from measurement of the fluid sample, determine component mole fractions of the fluid sample using a mole fraction distribution function, and determine calculated fluid properties using equation of state flash calculating.

These fluid characterization methods and/or systems for characterizing a fluid sample may include any of the various features of the compositions, methods, and systems disclosed herein. Without limitation, the methods and/or systems may further comprise operating a downhole fluid sampling tool in a wellbore to obtain the fluid sample. The methods and/or systems may further comprise wherein the fluid properties of the input parameters comprise a component concentration, a live oil density, and a gas-to-oil ratio. The methods and/or systems may further comprise wherein the component concentration is a lumped component concentration. The methods and/or systems may further comprise obtaining initial values for molecular weight of C6+ components and density of C36+ components of the fluid sample. The methods and/or systems may further comprise wherein the initial values are used in the mole fraction distribution function to determine component mole fractions. The methods and/or systems may further comprise wherein the component mole fractions determined using the mole fraction distribution function are delumped component mole fractions of a lumped component concentration obtained in the step of analyzing the fluid sample. The methods and/or systems may further comprise wherein the mole fraction distribution function is represented by equation (1). The methods and/or systems may further comprise wherein the step of determining component mole fractions of the fluid sample comprises solving the mole fraction distribution function for one or more unknown parameters. The methods and/or systems may further comprise wherein the step of determining component mole fractions of the fluid sample further comprises determining the component mole fractions of the fluid sample based on the mole fraction distribution function. The methods and/or systems may further comprise comparing the calculated fluid properties with the input parameters, the calculated fluid properties and input parameters comprising gas-to-ratio and dead oil density. The methods and/or systems may further comprise determining updated values for molecular weight of C6+ components and density of C36+ components of the fluid sample if the difference in the calculated fluid properties are not within a tolerance error, and then repeating the steps of determining component mole fractions and determining calculated fluid properties. The methods and/or systems may further comprise wherein the downhole fluid sampling tool comprising an elongated tool body and a sensor. The methods and/or systems may further comprise wherein the processing unit is distributed between a downhole processing unit and a processing unit disposed at a surface.

EXAMPLES

To facilitate a better understanding of the present technique, the following examples of some specific embodiments are given. In no way should the following examples be read to limit, or to define, the scope of the invention.

Techniques disclosed herein were used to characterize six different oil samples. The oil samples had varying gas-to-oil ratios from 100 to 2000 cc/cc. The predicted component mole fractions from fluid characterization method 156 were compared with laboratory-measured gas-chromatograph data. First, the full-length fluid compositions from the gas-chromatograph report were lumped into components of $CO_2$, C1, C2, C3, C4-5, and C6+, in weight percentage to simulate the measurement results of a downhole tool. These may be referred to as pseudo-tool data. The pseudo-tool data along with the gas-to-oil ratio and dead oil density may then be used as the input fluid properties derived in step 160 of FIG. 3. Based on the gas-to-oil ratio and dead-oil density, the pseudo-tool data may be delumped and characterized in steps 162 to 170 and then repeated until the tolerance error is satisfied. The delumped component mole fractions for the six oil samples are compared to the gas-chromatograph data in FIGS. 6A to 6F. Carbon number 36 denotes the 36+ fraction. As can be seen from FIGS. 6A to 6F, the delumped component mole fractions and gas-chromatograph data are in good agreement. Further, the delumped component mole fractions and the gas-chromatograph data may be used to generate the phase envelope. FIGS. 7A to 7F illustrate a comparison of the phase envelope predictions derived from the delumped component mole fractions and the gas-chromatograph data. As can be seen from FIGS. 7A to 7F, the phase envelope predictions are in good agreement for the delumped component mole fractions and the gas-chromatograph data. At reservoir conditions, bubble point may be a consideration. Accordingly, FIGS. 8A to 8F illustrate a comparison of the relative error between the saturated pressure at 250° F. predicted for delumped component mole fractions and the gas-chromatograph data. It is noted that generally the relative error increases as the gas-to-oil ratio of the fluid increases. The maximum error was around 5%.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A fluid characterization method comprising:
obtaining a fluid sample of a reservoir fluid;
analyzing the fluid sample to derive input parameters, wherein the input parameters comprise fluid properties obtained from measurement of the fluid sample;
determining component mole fractions of the fluid sample using a mole fraction distribution function;
determining calculated fluid properties using equation of state flash calculating; and
determining updated values for molecular weight of C6+ components and density of C36+ components of the fluid sample if a difference in the calculated fluid properties are not within a tolerance error, and then repeating the steps of determining component mole fractions and determining calculated fluid properties.

2. The method of claim 1, wherein obtaining the fluid sample comprising operating a downhole fluid sampling tool in a wellbore to obtain the fluid sample.

3. The method of claim 1, wherein the fluid properties of the input parameters comprise a component concentration, a live oil density, and a gas-to-oil ratio.

4. The method of claim 3, wherein the component concentration is a lumped component concentration.

5. The method of claim 1, further comprising obtaining initial values for molecular weight of C6+ components and density of C36+ components of the fluid sample.

6. The method of claim 5, wherein the initial values are used in the mole fraction distribution function to determine component mole fractions.

7. The method of claim 1, wherein the component mole fractions determined using the mole fraction distribution function are delumped component mole fractions of a lumped component concentration obtained in the step of analyzing the fluid sample.

8. The method of claim 1, wherein the mole fraction distribution function is represented by the following equation:

$$z_i = \begin{cases} \sigma e^{-\tau_1(k-i)^{\alpha_1}}, & i = 5, \ldots, k \\ \sigma e^{-\tau_1(k-i)^{\alpha_1}}, & i = k, \ldots, 200 \end{cases}$$

wherein i is single carbon number, z is mole fraction of component with single carbon number i, k is single carbon number with local maximum mole fraction, and G1, 02, T1, T2, and a are unknown parameters to be solved.

9. The method of claim 1, wherein the step of determining component mole fractions of the fluid sample comprises solving the mole fraction distribution function for one or more unknown parameters.

10. The method of claim 9, wherein the step of determining component mole fractions of the fluid sample further comprises determining the component mole fractions of the fluid sample based on the mole fraction distribution function.

11. The method of claim 1, further comprising comparing the calculated fluid properties with the input parameters, the calculated fluid properties and input parameters comprising gas-to-ratio and dead oil density.

12. A system for characterizing a fluid sample, comprising:
a downhole fluid sampling tool operable to obtain fluid samples while disposed in a wellbore; and
a processing unit operable to:
analyze the fluid sample to derive input parameters, wherein the input parameters comprise fluid properties obtained from measurement of the fluid sample;
determine component mole fractions of the fluid sample using a mole fraction distribution function;
determine calculated fluid properties using equation of state flash calculating; and determine updated values for molecular weight of C6+ components and density of C36+ components of the fluid sample if the difference in the calculated fluid propeliies are not within a tolerance error.

13. The system of claim 12, wherein the downhole fluid sampling tool comprises an elongated tool body and a sensor.

14. The system of claim 12, wherein the processing unit is distributed between a downhole processing unit and a processing unit disposed at a surface.

15. The system claim 12, wherein the fluid properties of the input parameters comprise a component concentration, a live oil density, and a gas-to-oil ratio, and wherein the component concentration is a lumped component concentration.

16. The system of claim 12, wherein the processing unit is further operable to obtain initial values for molecular weight of C6+ components and density of C36+ components of the fluid sample, wherein the initial values are used in the mole fraction distribution function to determine component mole fractions.

17. The system of claim 12, wherein the mole fraction distribution function is represented by the following equation:

$$z_i = \begin{cases} \sigma e^{-\tau_1 (k-i)^{\alpha_1}}, & i = 5, \dots, k \\ \sigma e^{-\tau_1 (k-i)^{\alpha_1}}, & i = k, \dots, 200 \end{cases}$$

wherein i is single carbon number, z is mole fraction of component with single carbon number i, k is single carbon number with local maximum mole fraction, and 01, 02, 1\, 2, and a are unknown parameters to be solved.

18. The system of claim 12, wherein the processing unit is further operable to compare the calculated fluid properties with the input parameters, the calculated fluid properties and input parameters comprising gas-to-ratio and dead oil density.

* * * * *